United States Patent
Okabe

(10) Patent No.: US 9,616,082 B2
(45) Date of Patent: *Apr. 11, 2017

(54) ANTITUMOR AGENT INCLUDING IRINOTECAN HYDROCHLORIDE HYDRATE

(71) Applicant: TAIHO PHARMACEUTICAL CO., LTD., Chiyoda-ku (JP)

(72) Inventor: Hiroyuki Okabe, Hanno (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/780,269

(22) PCT Filed: Mar. 27, 2014

(86) PCT No.: PCT/JP2014/058732
§ 371 (c)(1),
(2) Date: Sep. 25, 2015

(87) PCT Pub. No.: WO2014/157443
PCT Pub. Date: Oct. 2, 2014

(65) Prior Publication Data
US 2016/0045530 A1    Feb. 18, 2016

(30) Foreign Application Priority Data
Mar. 27, 2013    (JP) .................... 2013-066073

(51) Int. Cl.
| | | |
|---|---|---|
| A01N 43/04 | (2006.01) | |
| A61K 31/70 | (2006.01) | |
| A61K 31/7072 | (2006.01) | |
| A61K 31/4745 | (2006.01) | |
| A61K 31/506 | (2006.01) | |
| A61K 31/513 | (2006.01) | |
| A61K 31/7064 | (2006.01) | |
| A61K 31/706 | (2006.01) | |
| A61K 31/7068 | (2006.01) | |

(52) U.S. Cl.
CPC ...... *A61K 31/7072* (2013.01); *A61K 31/4745* (2013.01); *A61K 31/506* (2013.01); *A61K 31/513* (2013.01); *A61K 31/706* (2013.01); *A61K 31/7064* (2013.01); *A61K 31/7068* (2013.01)

(58) Field of Classification Search
None
See application file for complete search history.

(56) References Cited

U.S. PATENT DOCUMENTS

| | | |
|---|---|---|
| 7,799,783 B2 | 9/2010 | Emura et al. |
| 2016/0082031 A1 | 3/2016 | Okabe |

FOREIGN PATENT DOCUMENTS

WO    2006/080327 A1    8/2006

OTHER PUBLICATIONS

Ishida et al. Mol Cancer Ther Nov. 2013 (12) (11 Supplement) B87; DOI: 10.1158/1535-7163.TARG-13-B87.*
Michael J. Overman, et al., "Phase 1 study of TAS-102 administered once daily on a 5-day-per-week schedule in patients with solid tumors," Invest New Drugs (2008), vol. 26, May 2008, pp. 445-454.
Takayuki Yoshino, et al., "TAS-102 monotherapy for pretreated metastatic colorectal cancer: a double-blind, randomized, placebo-controlled phase 2 trial," Lancet Oncology, vol. 13, Oct. 2012, pp. 993-1001.
Mace L. Rothenberg, "Irinotecan (CPT-11): Recent Developments and Future Directions—Colorectal Cancer and Beyond," The Oncologist, vol. 6(1), 2001, pp. 66-80.
Olaf H. Temmink, et al., "Irinotecan-induced cytotoxicity to colon cancer cells in vitro is stimulated by pre-incubation with trifluorothymidine," European Journal of Cancer, vol. 43, 2007, pp. 175-183.
Ayumu Goto, "Current Evidence of Irinotecan Combination Chemotherapy with TS-1 in Patients with Advanced Colorectal Cancer," Japan Journal of Cancer and Chemotherapy, vol. 33, No. 7, Jul. 2006, pp. 896-900 (with English abstract).
Sotaro Sadahiro, et al., "Two Patients with Recurrent Colon Cancer Who Underwent Surgery Following a Combination of Irinotecan and UFT," Japan Journal of Cancer and Chemotherapy, vol. 29, No. 11, Nov. 2002, pp. 2013-2018 (with English abstract).
K. Yamazaki, et al., "A first combination phase I study of TAS-102 and irinotecan (Iri) in Japanese patients (pts) with metastatic colorectal cancer (mCRC) refractory to fluoropyrimidine (FU) and oxaliplatin (Ox)," European Journal of Cancer, vol. 49, Suppl. 2, Sep. 2013 (3 pages).
Olaf H. Temmink, et al., "Therapeutic potential of the dual-targeted TAS-102 formulation in the treatment of gastrointestinal malignancies," Cancer Sci., vol. 98, No. 6, Jun. 2007, pp. 779-789.
International Search Report issued Jun. 17, 2014 in PCT/JP2014/058732 filed Mar. 27, 2014.

* cited by examiner

*Primary Examiner* — Patrick Lewis
(74) *Attorney, Agent, or Firm* — Oblon, McClelland, Maier & Neustadt, L.L.P.

(57) ABSTRACT

Provided is a novel combination therapy using an FTD/TPI combination drug which exhibits remarkable antitumor effects, and few side effects.
An antitumor agent is characterized in that one cycle of an administration schedule, in which, in a period of 14 days, the FTD/TPI combination drug is administered on days 1 to 5, and CPT-11 is administered on day 1, is repeated at least once.

21 Claims, 5 Drawing Sheets

US 9,616,082 B2

ANTITUMOR AGENT INCLUDING IRINOTECAN HYDROCHLORIDE HYDRATE

TECHNICAL FIELD

The present invention relates to an antitumour agent using a trifluridine/tipiracil hydrochloride combination drug in combination with irinotecan hydrochloride hydrate, and to an enhancer for the antitumor effect of irinotecan hydrochloride hydrate.

BACKGROUND ART

Trifluridine (also called: α,α,α-trifluorothymidine. Hereinafter, also referred to as "FTD") exerts an antitumor effect due to an action for inhibiting thymidylate formation and an action for inhibiting DNA synthesis by incorporation into DNA. On the other hand, tipiracil hydrochloride (chemical name: 5-chloro-6-[(2-iminopyrrolidin-1-yl)methyl]-pyrimidine-2,4(1H,3H)-dione hydrochloride. Hereinafter, also referred to as "TPI") has an action for inhibiting thymidine phosphorylase. It is known that the antitumor effect of FTD is enhanced by the TPI suppressing the degradation of FTD in vivo caused by thymidine phosphorylase (Patent Literature 1). Currently, an antitumor agent containing FTD and TPI in a molar ratio of 1:0.5 (hereinafter referred to as "FTD/TPI combination drug") is under development as a therapeutic agent for solid cancers, for example, colorectal cancer (Non Patent Literatures 1 and 2).

Further, irinotecan hydrochloride hydrate (hereinafter, also referred to as "CPT-11") is a camptothecin derivative whose active metabolite is SN-38 and which suppresses the synthesis and transcription of DNA by inhibiting topoisomerase I, thereby to exert an antitumor effect. CPT-11 is clinically used as a therapeutic agent for a wide range of cancer types including, for example, small cell lung cancer, non-small cell lung cancer, cervical cancer, ovarian cancer, gastric cancer, colorectal cancer, breast cancer, squamous cell carcinoma, and malignant lymphoma (Non Patent Literature 3).

Further, when FTD and SN-38 were allowed to act on a colorectal cancer cell line, a synergistic cytotoxicity was observed and thus a combination therapy using an FTD/TPI combination drug and CPT-11 has been expected (Non Patent Literature 4).

CITATION LIST

Patent Literature

Patent Literature 1: WO 96/30346

Non Patent Literature

Non Patent Literature 1: Invest New Drugs 26 (5): 445-54, 2008.
Non Patent Literature 2: Lancet Oncol. 13 (10): 993-1001, 2012.
Non Patent Literature 3: Oncologist. 6(1): 66-80, 2001.
Non Patent Literature 4: Eur J Cancer. 43(1): 175-83, 2007.

SUMMARY OF INVENTION

Technical Problem

The object of the present invention is to provide a novel combination therapy for solid cancers using an FTD/TPI combination drug which exhibits remarkable antitumor effects, and few side effects.

Solution to Problem

In view of this situation, when a combination therapy comprising repeating a 28-day cycle consisting of two times of 5-days' administration with 2-days' rest of an FTD/TPI combination drug, followed by rest of the drug administration for 2 weeks, and an administration of CPT-11 once in 2 weeks was performed in a colorectal cancer patient on the basis of an administration schedule in which effects of each drug have previously been reported as in Reference Example described later, only about 30% of the predetermined amount of CPT-11 could be administered because side effects appeared strongly. Since antitumor effect is generally proportional to the total dose, the present inventors have studied on administration schedule which can suppress the occurrence of side effects and in which a predetermined amount can be administered. As a result, the present inventors have found that a combination therapy comprising repeating one cycle administration schedule, in which, in a period of 14 days, an FTD/TPI combination drug is administered to a solid cancer patient (particularly colorectal cancer patient) for 5 days, followed by rest of the drug administration for 9 days, and CPT-11 is administered once in 2 weeks, can suppress the occurrence of side effects, for example, neutropenia, diarrhea and body weight loss, can administer a predetermined amount and exert an excellent antitumor effects.

That is, the present invention provides the following inventions [1] to [26].

[1] An antitumor agent for solid cancers, wherein one cycle of an administration schedule, in which, in a period of 14 days, a combination drug containing trifluridine and tipiracil hydrochloride in a molar ratio of 1:0.5 is administered at a dose of 20 to 80 mg/m$^2$/day using a reduced amount of trifluridine on Days 1 to 5 and irinotecan hydrochloride hydrate is administered at a dose of 50 to 200 mg/m$^2$/day on Day 1, is repeated once or twice or more times.

[2] The antitumor agent according to [1], wherein the combination drug containing trifluridine and tipiracil hydrochloride in a molar ratio of 1:0.5 is administered at a dose of 40 to 70 mg/m$^2$/day using a reduced amount of trifluridine.

[3] The antitumor agent according to [1] or [2], wherein irinotecan hydrochloride hydrate is administered at a dose of 100 to 180 mg/m$^2$/day.

[4] The antitumor agent according to any one of [1] to [3], wherein the solid cancer is colorectal cancer, lung cancer, breast cancer, pancreatic cancer, or gastric cancer.

[5] An antitumor effect enhancer comprising a combination drug containing trifluridine and tipiracil hydrochloride in a molar ratio of 1:0.5 for enhancing the antitumor effect of irinotecan hydrochloride hydrate in a solid cancer patient, wherein one cycle of an administration schedule, in which, in a period of 14 days, the combination drug containing trifluridine and tipiracil hydrochloride in a molar ratio of 1:0.5 is administered at a dose of 20 to 80 mg/m$^2$/day using a reduced amount of trifluridine on Days 1 to 5 and irinotecan hydrochloride hydrate is administered at a dose of 50 to 200 mg/m$^2$/day on Day 1, is repeated once or twice or more times.

[6] An antitumor agent comprising a combination drug containing trifluridine and tipiracil hydrochloride in a molar ratio of 1:0.5 for treating a solid cancer patient who has received irinotecan hydrochloride hydrate, wherein one cycle of an administration schedule, in which, in a period of 14 days, the combination drug containing trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1, is repeated once or twice or more times.

[7] A kit preparation comprising an antitumor agent containing a combination drug of trifluridine and tipiracil hydrochloride in a molar ratio of 1:0.5 and an instruction for use, wherein the instruction for use describes one cycle of an administration schedule to a solid cancer patient, in which, in a period of 14 days, the combination drug containing trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1.

[8] A combination drug comprising trifluridine and tipiracil hydrochloride in a molar ratio of 1:0.5 for treating a solid cancer, wherein one cycle of an administration schedule, in which, in a period of 14 days, the combination drug comprising trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1, is repeated once or twice or more times.

[9] The combination drug according to [8], wherein the combination drug comprising trifluridine and tipiracil hydrochloride in a molar ratio of 1:0.5 is administered at a dose of 40 to 70 mg/m²/day using a reduced amount of trifluridine.

[10] The combination drug according to [8] or [9], wherein irinotecan hydrochloride hydrate is administered at a dose of 100 to 180 mg/m²/day.

[11] The combination drug according to any one of [8] to [10], wherein the solid cancer is colorectal cancer, lung cancer, breast cancer, pancreatic cancer, or gastric cancer.

[12] A combination drug comprising trifluridine and tipiracil hydrochloride in a molar ratio of 1:0.5 for enhancing the antitumor effect of irinotecan hydrochloride hydrate in a solid cancer patient, wherein one cycle of an administration schedule, in which, in a period of 14 days, the combination drug comprising trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1, is repeated once or twice or more times.

[13] A combination drug comprising trifluridine and tipiracil hydrochloride in a molar ratio of 1:0.5 for treating a solid cancer patient who has received irinotecan hydrochloride hydrate, wherein one cycle of an administration schedule, in which, in a period of 14 days, the combination drug comprising trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1, is repeated once or twice or more times.

[14] Use of a combination drug comprising trifluridine and tipiracil hydrochloride in a molar ratio of 1:0.5 for manufacturing an antitumor agent against solid cancers, wherein one cycle of an administration schedule, in which, in a period of 14 days, the combination drug comprising trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1, is repeated once or twice or more times.

[15] The use according to [14], wherein the combination drug comprising trifluridine and tipiracil hydrochloride in a molar ratio of 1:0.5 is administered at a dose of 40 to 70 mg/m²/day using a reduced amount of trifluridine.

[16] The use according to [14] or [15], wherein irinotecan hydrochloride hydrate is administered at a dose of 100 to 180 mg/m²/day.

[17] The use according to anyone of [14] to [16], wherein the solid cancer is colorectal cancer, lung cancer, breast cancer, pancreatic cancer, or gastric cancer.

[18] Use for manufacturing an antitumor effect enhancer comprising a combination drug containing trifluridine and tipiracil hydrochloride in a molar ratio of 1:0.5 to enhance the antitumor effect of irinotecan hydrochloride hydrate in a solid cancer patient, wherein one cycle of an administration schedule, in which, in a period of 14 days, the combination drug containing trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1, is repeated once or twice or more times.

[19] Use for manufacturing an antitumor agent comprising a combination drug containing trifluridine and tipiracil hydrochloride in a molar ratio of 1:0.5 to treat a solid cancer patient who has received irinotecan hydrochloride hydrate, wherein one cycle of an administration schedule, in which, in a period of 14 days, the combination drug containing trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1, is repeated once or twice or more times.

[20] A therapeutic method for solid cancers, comprising repeating one cycle of an administration schedule to a solid cancer patient once or twice or more times, wherein in a period of 14 days, a combination drug containing trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1.

[21] The method according to [20], wherein the combination drug comprising trifluridine and tipiracil hydrochloride in a molar ratio of 1:0.5 is administered at a dose of 40 to 70 mg/m²/day using a reduced amount of trifluridine.

[22] The method according to [20] or [21], wherein irinotecan hydrochloride hydrate is administered at a dose of 100 to 180 mg/m²/day.

[23] The method according to any one of [20] to [22], wherein the solid cancer is colorectal cancer, lung cancer, breast cancer, pancreatic cancer, or gastric cancer.

[24] A method for enhancing an antitumor effect of irinotecan hydrochloride hydrate in a solid cancer patient, comprising repeating one cycle of an administration schedule once or twice or more times, wherein in a period of 14 days, the combination drug containing trifluridine and tipiracil hydrochloride in a molar ratio of 1:0.5 is administered at a dose of 20 to 80 mg/m²/day using a reduced amount of trifluridine on Days 1 to 5 and irinotecan hydrochloride hydrate is administered at a dose of 50 to 200 mg/m²/day on Day 1.

[25] A method for treating a solid cancer patient who has received irinotecan hydrochloride hydrate, comprising administering a combination drug containing trifluridine and tipiracil hydrochloride in a molar ratio of 1:0.5 at a dose of 20 to 80 mg/m$^2$/day using a reduced amount of trifluridine on Days 1 to 5 and repeating one cycle of an administration schedule once or twice or more times, in which, in a period of 14 days, irinotecan hydrochloride hydrate is administered at a dose of 50 to 200 mg/m$^2$/day on Day 1.

[26] An antitumor agent for solid cancers, wherein one cycle of an administration schedule, in which, in a period of 14 days, a combination drug comprising trifluridine and tipiracil hydrochloride in a molar ratio of 1:0.5 is administered on Days 1 to 5 at the recommended dose in the monotherapy for the combination drug comprising trifluridine and tipiracil hydrochloride in a molar ratio of 1:0.5 and irinotecan hydrochloride hydrate is administered on Day 1 at the recommended dose in the monotherapy for irinotecan hydrochloride hydrate, is repeated once or twice or more times.

Advantageous Effects of Invention

According to the antitumor agent of the present invention, it is possible to perform cancer treatment exhibiting a high antitumor effect while suppressing the onset of side effects, thereby achieving long-term survival in patients.

DESCRIPTION OF EMBODIMENTS

Figure 1:
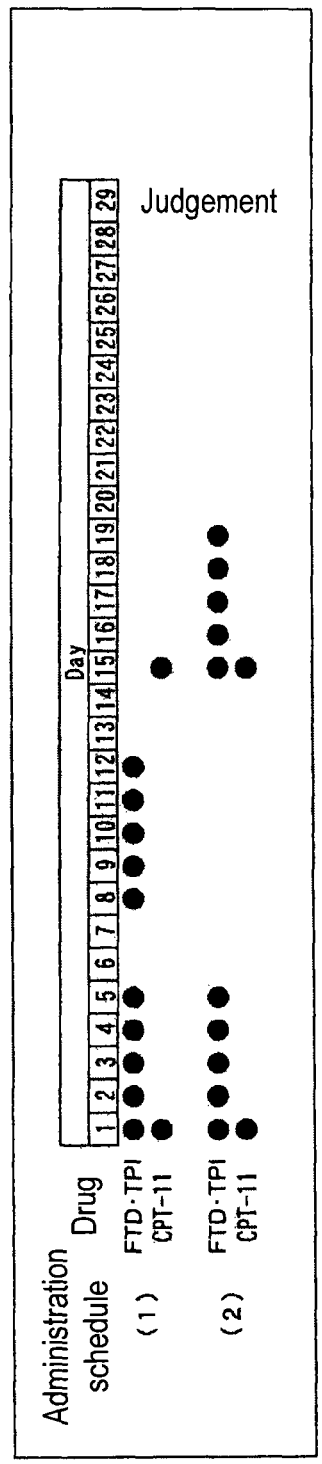
FIG. 1 is a diagram illustrating administration schedules (1) and (2). The black circle indicates the day of administration.

FTD and TPI of the present invention are both known compounds and can be synthesized, for example, according to the method described in WO 96/30346. A combination drug of FTD and TPI in a molar ratio of 1:0.5 is also known (Non Patent Literatures 1 and 2).

CPT-11 of the present invention is a known compound and can be synthesized according to the method described in Japanese Patent No. 3,004,077. Also, the commercially available product, for example, CAMPTO (registered trademark, Yakult Honsha Co., Ltd.), may be used.

The antitumor agent of the present invention is characterized in that one cycle of an administration schedule, in which, in a period of 14 days, a combination drug comprising FTD and TPI in a molar ratio of 1:0.5 is administered on Days 1 to 5 and irinotecan hydrochloride hydrate is administered on Day 1, is repeated once or twice or more times.

As shown in Reference Example and Examples described below, when the recommended dose of FTD/TPI combination drug in the monotherapy in mice and the recommended dose of CPT-11 in the monotherapy in mice were administered in combination to mice in accordance with the administration schedule, superior antitumor effects as well as suppression of side effects could be achieved. Thus, it is clear that the dose of FTD/TPI combination drug and CPT-11 in humans according to the administration schedule of the present invention is equivalent to the recommended dose of FTD/TPI combination drug and CPT-11 in humans in the monotherapy.

In other words, the dose of FTD on Days 1 to 5 is 20 to 80 mg/m$^2$/day, and from the viewpoint of a balance between antitumor effects and side effects, the dose of FTD is more preferably 40 to 70 mg/m$^2$/day, especially preferably 70 mg/m$^2$/day.

The dose of CPT-11 on Day 1 is 50 to 200 mg/m$^2$/day using a reduced amount of irinotecan hydrochloride hydrate, and from the viewpoint of a balance between antitumor effects and side effects, the dose of CPT-11 is preferably 100 to 180 mg/m$^2$/day, more preferably 150 to 180 mg/m$^2$/day, especially preferably 180 mg/m$^2$/day.

The target of the antitumor agent of the present invention is directed to solid tumors, including specifically head and neck cancer, gastrointestinal cancer (esophageal cancer, gastric cancer, duodenal cancer, liver cancer, biliary tract cancer (gallbladder/bile duct cancer), pancreatic cancer, small intestinal cancer, large intestinal cancer (colorectal cancer, colon cancer, rectal cancer), etc.), lung cancer, breast cancer, ovarian cancer, uterine cancer (cervical cancer, endometrial cancer), renal cancer, bladder cancer, prostate cancer, etc. Of these, from the viewpoint of antitumor effects and side effects, the target of the antitumor agent of the present invention is preferably gastrointestinal cancer, lung cancer, or breast cancer, more preferably colorectal cancer, pancreatic cancer, gastric cancer, lung cancer, or breast cancer, more preferably colorectal cancer and gastric cancer, and especially preferably colorectal cancer. Here, the solid cancer includes not only a primary tumor but also a tumor derived from a solid cancer that has metastasized to other organs (such as liver). Also, the antitumor agent of the present invention may be one used for postoperative adjuvant chemotherapy that is performed for preventing the recurrence after having extracted the tumor surgically.

Since the administration schedule is different in each active ingredient, all the active ingredients cannot be formulated into one dosage form. Thus, the antitumor agent of the present invention is separately formulated into a plurality of dosage forms for each active ingredient. It is preferred that FTD and TPI are formulated as a combination drug and CPT-11 is formulated as a single agent.

In addition, as long as each active ingredient is administered according to the administration schedule of the present invention, each preparation may be manufactured and sold together in a single package suitable for combined administration, or each preparation may be manufactured and sold after being divided into a separate package.

There is no particular limitation to the dosage form of the antitumor agent of the present invention, and it can be appropriately selected depending on the therapeutic purposes and includes specifically oral preparations (tablets, coated tablets, powders, granules, capsules, solutions, etc.), injections, suppositories, patches, ointments, etc. An oral preparation is preferable for the combination drug of FTD and TPI, and an injectable preparation is preferable for CPT-11.

Depending on the dosage form, the antitumor agent of the present invention can be usually prepared by the known method using a pharmaceutically acceptable carrier. Such a carrier includes various ones which are commonly used in conventional drugs, such as excipients, binders, disintegrators, lubricants, diluents, solubilizers, suspending agents, isotonic agents, pH adjusting agents, buffering agents, stabilizers, coloring agents, flavoring agents, and flavors.

The present invention also relates to an antitumor effect enhancer comprising an FTD/TPI combination drug for enhancing the antitumor effect of CPT-11 in a solid cancer patient (especially colorectal cancer patient), wherein the FTD/TPI combination drug and CPT-11 are administered on the basis of the administration schedule described above. The antitumor effect enhancer has the dosage form of the above antitumor agent.

In addition, the present invention relates to an antitumor agent comprising an FTD/TPI combination drug for treating a cancer patient (especially colorectal cancer patient) who has received CPT-11, wherein the FTD/TPI combination drug and CPT-11 are administered on the basis of the administration schedule described above. The antitumor agent has the above dosage form.

Further, the present invention relates to a kit preparation comprising an FTD/TPI combination drug and an instruction for use teaching that the FTD/TPI combination drug and CPT-11 are to be administered based on the administration schedule. Here, the term "instruction for use" may be any one as long as it describes the administration schedule; however, an instruction for use, in which the administration schedule is recommended though legal binding force does not matter, is preferable. The instruction for use includes specifically a package insert, a pamphlet, etc. Also, a kit preparation comprising an instruction for use may be one in which an instruction for use is printed on or attached to the package of the kit preparation, or may be one in which an antitumor agent together with an instruction for use is enclosed in a package of the kit preparation.

EXAMPLES

Then, the present invention is explained in more detail by way of Examples.
Reference Example Cultured cells ($1\times10^7$ cells/mouse) of human colon cancer cell line (KM20C) were intraperitoneally transplanted into 5-6 weeks old BALB/cA Jcl-nu mice after birth, and the mice were assigned to each group so that the mean body weight of each group became equal. The date on which such grouping (n=10) was performed was taken as Day 0.

An FTD/TPI combination drug (a mixture of FTD and TPI in a molar ratio of 1:0.5) was prepared so as to be 75, 100, 150, 300, and 450 mg/kg/day as FTD. Since a death case of irinotecan hydrochloride hydrate (CPT-11: CAMPTO (registered trademark) infusion, Yakult Honsha Co., Ltd.) at a dose of 111 mg/kg/day was reported (Kiso to Rinsho, (1990), Vol. 24, No. 14, 7-17), irinotecan hydrochloride hydrate was prepared so as to be 80 and 100 mg/kg/day. Starting the dug administration from Day 3, a 5-days' daily oral administration of the FTD/TPI combination drug with 2-days' rest was performed for 6 weeks, and CPT-11 was administered once in a week from the tail vein for 6 weeks.

As an index of the antitumor effect, the number of survivors of each group of mice and the survival time of each group was compared. The results are shown in Table 1.

TABLE 1

| Drug | Dose (mg/kg/day) | Treatment[a] | No. of animals | Survival time (day) Mean ± SD | ILS[b] (%) |
|---|---|---|---|---|---|
| Control | — | — | 10 | 40.0 ± 4.3 | — |
| FTD•TPI | 75 | 5-days' oral admistration with 2-days' rest (b.i.d) | 10 | 50.0 ± 9.1 | 25.0 |
| FTD•TPI | 100 | 5-days' oral admistration with 2-days' rest (b.i.d) | 10 | 75.8 ± 42.6 | 89.5 |
| FTD•TPI | 150 | 5-days' oral admistration with 2-days' rest (b.i.d) | 10 | 125.7 ± 64.8 | 214.3 |
| FTD•TPI | 300 | 5-days' oral admistration with 2-days' rest (b.i.d) | 10 | 75.6 ± 17.5 | 89.0 |
| FTD•TPI | 450 | 5-days' oral admistration with 2-days' rest (b.i.d) | 10 | 54.1 ± 18.3 | 35.3 |
| CTP-11 | 80 | i.v., weekly | 10 | 61.6 ± 12.6 | 54.0 |
| CTP-11 | 100 | i.v., weekly | 10 | 72.5 ± 12.3 | 81.3 |

[a]Drugs were given for 6 weeks from Day 3.
[b]ILS means increase in life span.
ILS(%) = [(mean survival time of treatment group)/(mean survival time of control group) − 1] × 100

As described in Table 1, since the 100 mg/kg/day administration group of CPT-11 had a long life span in mice, the recommended dose (RD) of CPT-11 in mice was 100 mg/kg/day. Thus, the dose of 100 mg/kg/day in mice is equivalent to RD of 150 to 180 mg/m²/day in humans.

Since life span is long in the administration group of 150 mg/kg/day of the FTD/TPI combination drug using a reduced amount of FTD, RD of the FTD/TPI combination drug in mice is 150 mg/kg/day using a reduced amount of FTD. Thus, the dose of 150 mg/kg/day (using a reduced amount of FTD) in mice is equivalent to RD of 70 mg/m²/day in humans.

Example 1

Human colon cancer cell lines (KM20C) were transplanted into the right chest of 5-6 weeks old BALB/cA Jcl-nu mice after birth. After tumor transplant, the major axis (mm) and minor axis (mm) of tumor were measured, and the tumor volume (TV) was calculated. Then, the animals were assigned to each group so that the mean TV of each group becomes equal and the day when grouping (n=6) was performed was taken as Day 0.

An FTD/TPI combination drug (a mixture of FTD and TPI in a molar ratio of 1:0.5) was prepared so as to be 150 mg/kg/day as FTD. Irinotecan hydrochloride hydrate (CPT-11: CAMPTO (registered trademark) infusion, Yakult Honsha Co., Ltd.) was prepared so as to be 100 mg/kg/day as irinotecan hydrochloride hydrate. In the administration schedule (1), the FTD/TPI combination drug was orally administered daily on Days 1-5 and on Days 8-12, and CPT-11 was administered via the tail vein on Days 1 and 15.

In the administration schedule (2), the FTD/TPI combination drug was orally administered daily on Days 1-5 and on Days 15-19, and CPT-11 was administered via the tail vein on Days 1 and 15. The FTD/TPI combination drug and CPT-11 in the monotherapy group were respectively administered at the same dose as the corresponding drugs according to the administration schedule in the combined administration group (FIG. 1).

Figure 2:
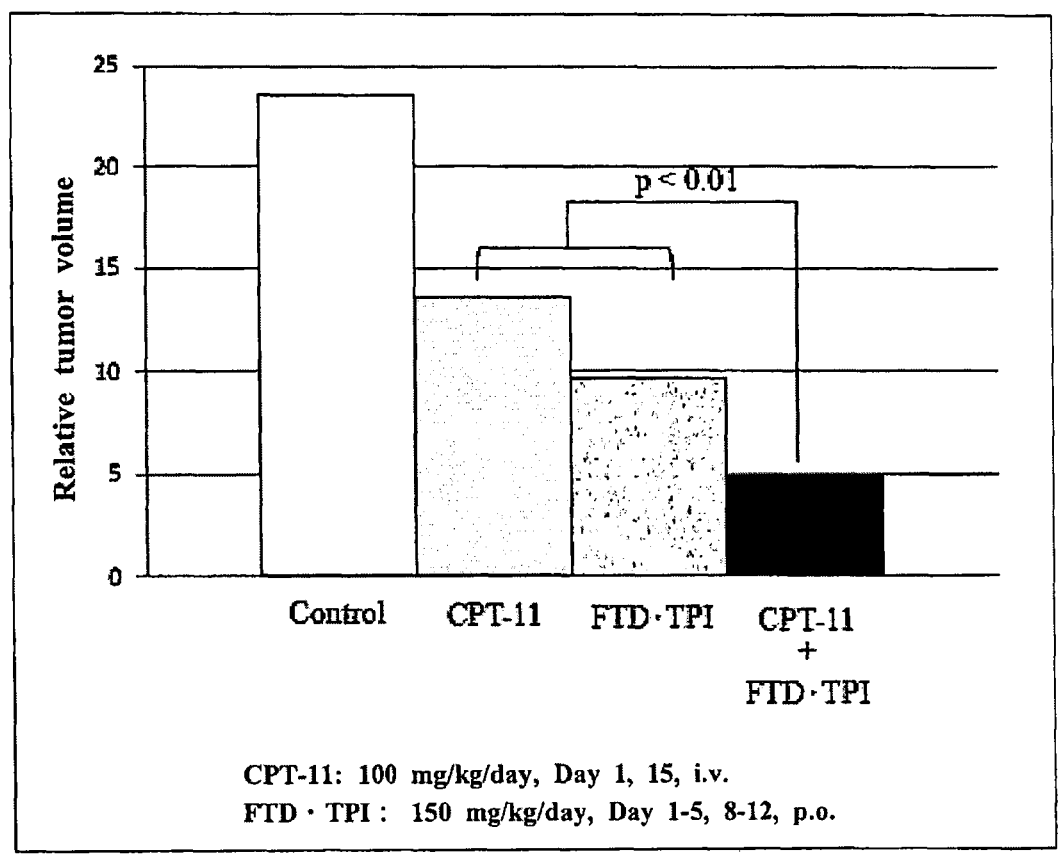
FIG. 2 is a graph illustrating an antitumor effect according to an administration schedule (1).
Figure 4:
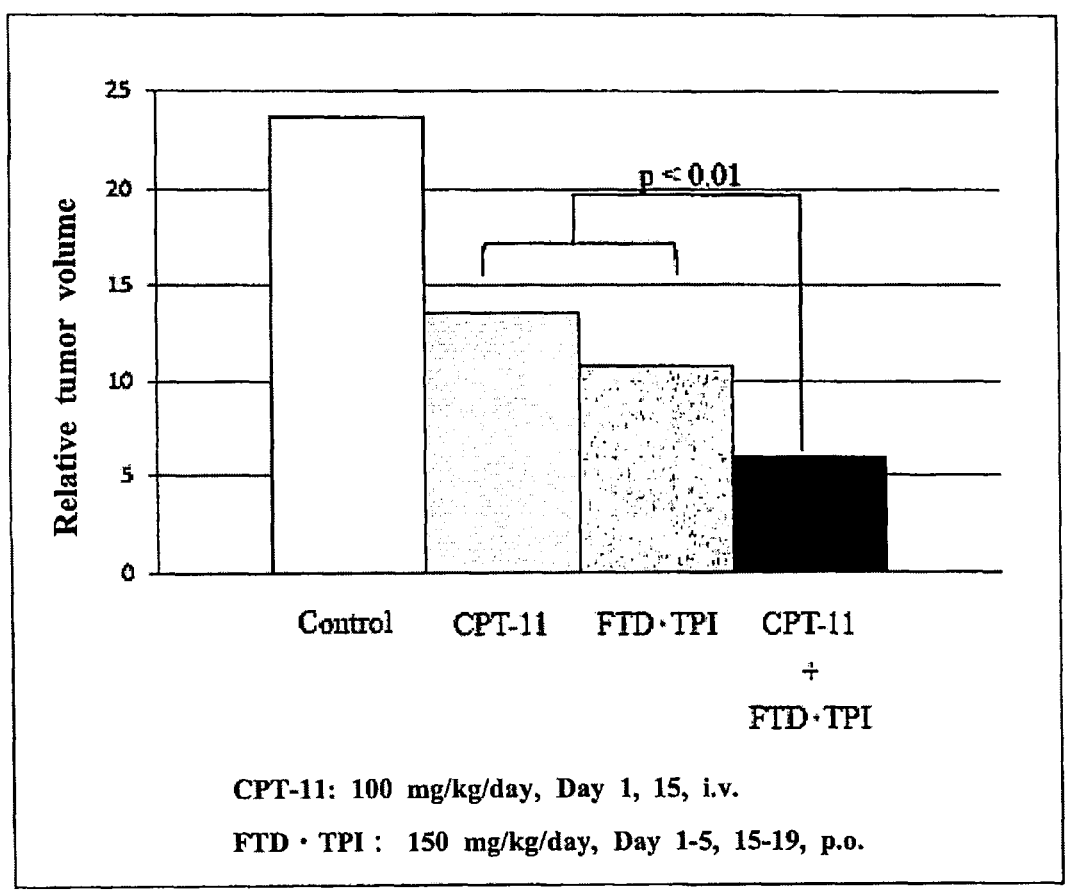
FIG. 4 is a graph illustrating an antitumor effect according to an administration schedule (2).

As an index of the antitumor effect, TV at Day 29 in each group was calculated and the relative tumor volume (RTV) at Day 0 was determined by the following formula and compared to RTV of the untreated group (control). Evaluation judgment on the combination effects was made as effective in the case where the mean RTV values of the combined administration group were statistically significantly lower (Welch's IUT, over all maximum p<0.05) than the mean RTV values of the individual monotherapy group. The results are shown in FIGS. 2 and 4. In the Figs, if the p-value is 0.05 or less, it shows that a statistically significant difference was observed in the monotherapy group.

$$TV\ (mm^3) = (long\ axis \times (short\ axis)^2)/2$$

$$RTV = (TV\ on\ Day\ 29)/(TV\ on\ Day\ 0)$$

Figure 3:
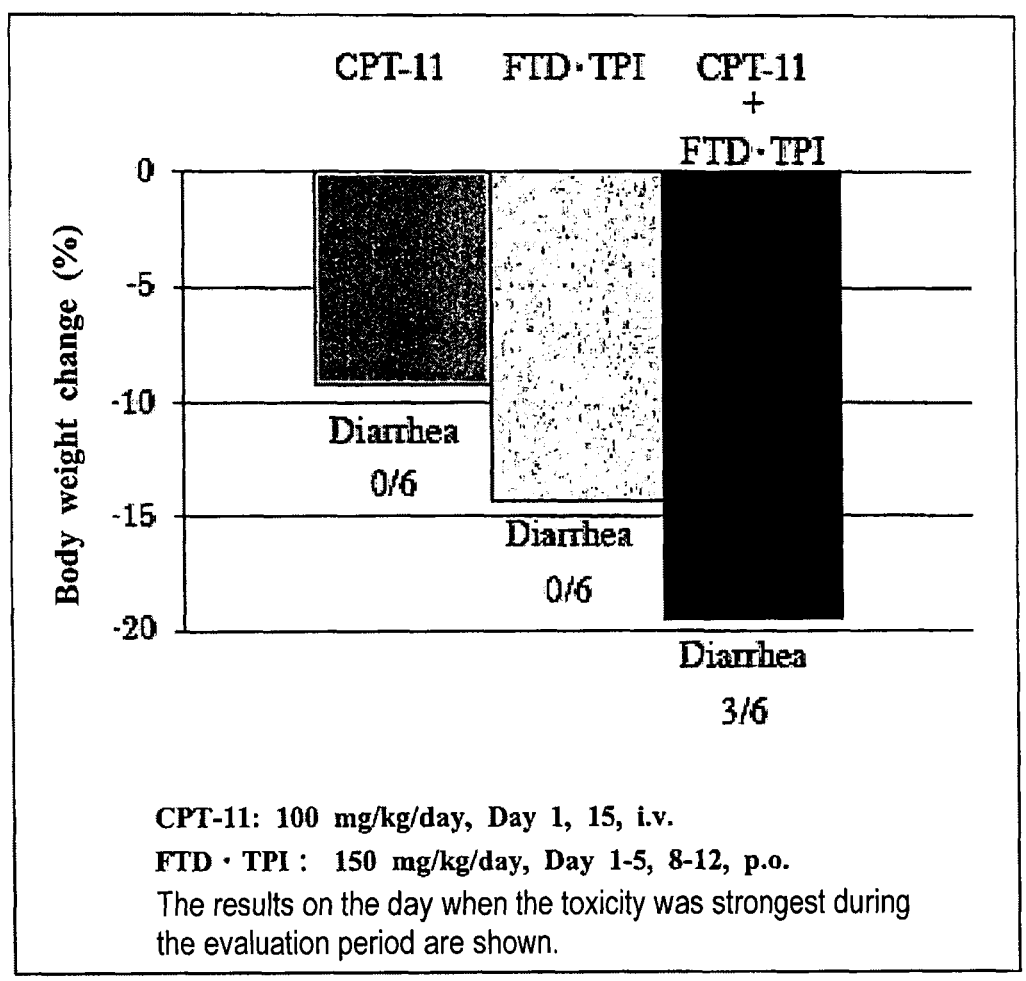
FIG. 3 is a graph illustrating a body weight change and an incidence of diarrhea according to an administration schedule (1).
Figure 5:
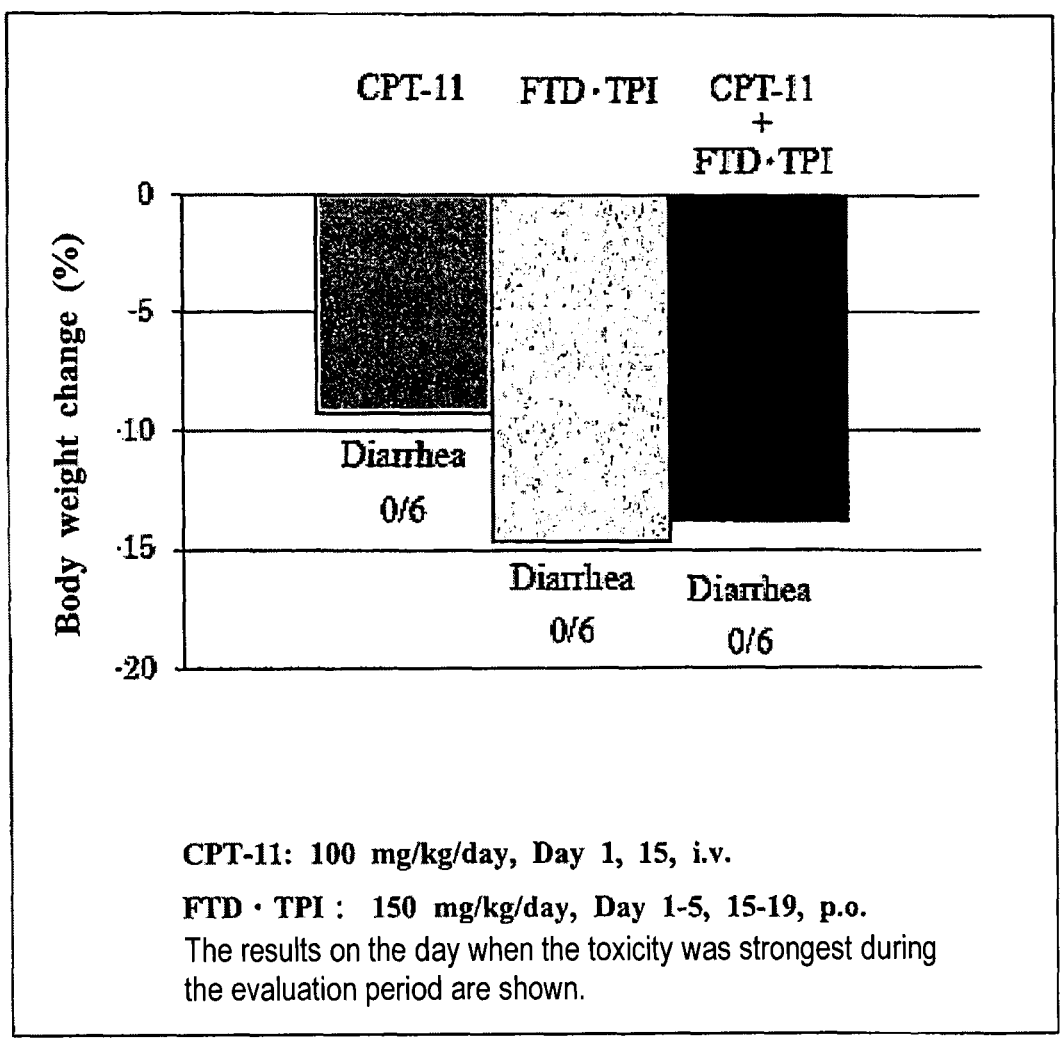
FIG. 5 is a graph illustrating a body weight change and an incidence of diarrhea according to an administration schedule (2).

In addition, the body weight (BW) was measured as an index of toxicity over time, the mean body weight change [BWC (%)] on Day n to the body weight on Day 0 was calculated by the following formula (n indicates the day when the body weight is measured twice in a week and the final measurement day corresponds to Day 29 that is the final evaluation day), and diarrhea was simultaneously observed in the individual mice during the test period. The results are shown in FIGS. 3 and 5.

From the results of FIGS. 2 to 5, it was revealed that the administration schedule (2) dramatically improved side effects such as body weight loss and diarrhea while maintaining the antitumor effects, in comparison with the administration schedule (1).

Example 2

A combined administration test of an FTD/TPI combination drug and CPT-11 was performed in the same manner as in Example 1, except that the cell line was changed to human gastric cancer cell line (SC-2). The FTD/TPI combination drug (a mixture of FTD and TPI in a molar ratio of 1:0.5) was prepared so as to be 75 and 150 mg/kg/day (recommended dose) as FTD, and CPT-11 was prepared so as to be 100 mg/kg/day (recommended dose) as irinotecan hydrochloride hydrate. The results are shown in Table 2.

As shown in Table 2, it was confirmed that the antitumor effect against gastric cancer was also significantly enhanced by the administration schedule (2). In addition, the body weight loss was within an acceptable range.

The invention claimed is:
1. A therapeutic method for a solid cancer, comprising:
    administering to a subject a combination drug comprising trifluridine and tipiracil hydrochloride in a molar ratio of 1:0.5 at a dose of 20 to 80 mg/m$^2$/day of trifluridine on Days 1 to 5 in a period of 14 days, and 50 to 200 mg/m$^2$/day of irinotecan hydrochloride hydrate on Day 1 in the period of 14 days.
2. The method according to claim 1, wherein the combination drug is administered at a dose of 40 to 70 mg/m$^2$/day of trifluridine.
3. The method according to claim 1, wherein 100 to 180 mg/m$^2$/day of irinotecan hydrochloride hydrate is administered.
4. The method according to claim 1, wherein the solid cancer is colorectal cancer, lung cancer, breast cancer, pancreatic cancer, or gastric cancer.
5. A method for enhancing an antitumor effect of irinotecan hydrochloride hydrate in a patient having a solid cancer, comprising:
    administering to the patient a combination drug comprising trifluridine and tipiracil hydrochloride in a molar ratio of 1:0.5 at a dose of 20 to 80 mg/m$^2$/day of trifluridine on Days 1 to 5 in a period of 14 days, and 50 to 200 mg/m$^2$/day of irinotecan hydrochloride hydrate on Day 1 in the period of 14 days.
6. A method for treating a patient having a solid cancer who has received irinotecan hydrochloride hydrate, comprising:
    administering to the patient a combination drug comprising trifluridine and tipiracil hydrochloride in a molar ratio of 1:0.5 at a dose of 20 to 80 mg/m$^2$/day of trifluridine on Days 1 to 5 in a period of 14 days, and 50 to 200 mg/m$^2$/day of irinotecan hydrochloride hydrate on Day 1 in the period of 14 days.
7. The method according to claim 1, wherein the period of 14 days is repeated a plurality of times.
8. The method according to claim 5, wherein the period of 14 days is repeated a plurality of times.
9. The method according to claim 6, wherein the period of 14 days is repeated a plurality of times.
10. The method according to claim 5, wherein the combination drug is administered at a dose of 40 to 70 mg/m$^2$/day of trifluridine.

TABLE 2

| Drug | Dose (mg/kg/day) | Treatment | RTV[a] (mean ± SD) | TGI[b] (%) |
|---|---|---|---|---|
| Control | — | — | 12.41 ± 0.65 | — |
| CPT-11 | 100 | Day 1, 15, i.v., q.d. | 2.70 ± 0.18** | 78.2 |
| FTD•TPI | 75 | Day 1~5, 15~19, p.o., b.i.d. | 8.77 ± 0.38** | 29.3 |
| FTD•TPI | 150 | | 7.30 ± 0.33** | 41.2 |
| FTD•TPI + CPT-11 | 75 + 100 | Day 1~5, 15~19, p.o., b.i.d. | 1.66 ± 0.22**,### | 86.6 |
| FTD•TPI + CPT-11 | 150 + 100 | Day 1, 15, i.v., q.d. | 1.29 ± 0.12**,### | 89.6 |

**p < 0.01 with Aspin-Welch's t-test as compared with the control group.
overall maximal p < 0.01 by closed testing procedure (Intersection-Union Test).
[a]Relative tumor volume (RTV) on Day 15 was calculated as the ratio of TV on Day 15 to that on Day 0 according to th RTV = (TV on Day 15)/(TV on Day 0)
[b]Tumor growth inhibition rate (TGI) on Day 15 on the basis of RTV was calculated according to the following formula TGI (%) = [1 − (mean RTV of the treated group)/(mean RTV of the control group)] × 100

11. The method according to claim 5, wherein 100 to 180 mg/m²/day of irinotecan hydrochloride hydrate is administered.

12. The method according to claim 5, wherein the solid cancer is colorectal cancer, lung cancer, breast cancer, pancreatic cancer, or gastric cancer.

13. The method according to claim 6, wherein the combination drug is administered at a dose of 40 to 70 mg/m²/day of trifluridine.

14. The method according to claim 6, wherein 100 to 180 mg/m²/day of irinotecan hydrochloride hydrate is administered.

15. The method according to claim 6, wherein the solid cancer is colorectal cancer, lung cancer, breast cancer, pancreatic cancer, or gastric cancer.

16. The method according to claim 1, wherein the solid cancer is colorectal cancer.

17. The method according to claim 5, wherein the solid cancer is colorectal cancer.

18. The method according to claim 6, wherein the solid cancer is colorectal cancer.

19. The method according to claim 1, wherein the combination drug is administered at a dose of 70 mg/m²/day of trifluridine.

20. The method according to claim 5, wherein the combination drug is administered at a dose of 70 mg/m²/day of trifluridine.

21. The method according to claim 6, wherein the combination drug is administered at a dose of 70 mg/m²/day of trifluridine.

* * * * *